(12) United States Patent
Kaska (10) Patent No.: US 8,286,637 B2
(45) Date of Patent: *Oct. 16, 2012

(54) STERILE RADIOLOGICAL IMAGING UNIT DRAPE AND METHOD OF PROVIDING A STERILE SURFACE THEREWITH

(76) Inventor: Serge Kaska, Encinitas, CA (US)

(*) Notice: Subject to any disclaimer, the term of this patent is extended or adjusted under 35 U.S.C. 154(b) by 273 days.

This patent is subject to a terminal disclaimer.

(21) Appl. No.: 12/835,165

(22) Filed: Jul. 13, 2010

(65) Prior Publication Data

US 2010/0275929 A1 Nov. 4, 2010

Related U.S. Application Data

(63) Continuation-in-part of application No. 12/248,291, filed on Oct. 9, 2008, now Pat. No. 8,042,549.

(60) Provisional application No. 61/043,644, filed on Apr. 9, 2008, provisional application No. 61/225,134, filed on Jul. 13, 2009.

(51) Int. Cl.
*A61B 19/08* (2006.01)
*H01J 35/16* (2006.01)
(52) U.S. Cl. ........................................ 128/852; 378/203
(58) Field of Classification Search .................. 128/846, 128/849, 852, 853, 854, 855, 856; 378/193, 378/203, 204
See application file for complete search history.

(56) References Cited

U.S. PATENT DOCUMENTS

| | | | |
|---|---|---|---|
| 3,791,382 A * | 2/1974 | Collins | 128/853 |
| 4,489,720 A | 12/1984 | Morris et al. | |
| 4,730,609 A | 3/1988 | McConnell | |
| 5,445,165 A | 8/1995 | Fenwick | |
| 7,044,132 B2 | 5/2006 | Masini | |
| 7,717,117 B2 | 5/2010 | Duarte | |
| 7,727,244 B2 | 6/2010 | Orban, III et al. | |
| 2006/0020152 A1 | 1/2006 | Theobald et al. | |
| 2008/0047567 A1 * | 2/2008 | Bonutti | 128/852 |

FOREIGN PATENT DOCUMENTS

WO 9638096 12/1996

* cited by examiner

*Primary Examiner* — Patricia Bianco
*Assistant Examiner* — Tarla Patel
(74) *Attorney, Agent, or Firm* — John D. Wright; Dickinson Wright PLLC (57) ABSTRACT

A surgical radiological C-arm imaging unit drape configured to provide a sterile outer surface about an end portion of a C-arm imaging unit and method of providing a sterile surface about an end of a C-arm imaging unit is provided. The drape includes a flexible enclosure having an upper wall with a pair of sidewalls and a rear side extending downwardly from the upper wall. The upper wall and the side walls are extendible between expanded and collapsed positions. When in the expanded position, a pocket sized for receipt of the end portion of the imaging unit beneath the upper wall is formed. The upper wall has a sterile outer surface configured to face away from and overlie the end portion of the imaging unit to maintain sterility in a sterile zone above an operating table. When in the collapsed position, the sterile outer surface shielded from external contamination.

29 Claims, 11 Drawing Sheets

STERILE RADIOLOGICAL IMAGING UNIT DRAPE AND METHOD OF PROVIDING A STERILE SURFACE THEREWITH

CROSS-REFERENCE TO RELATED APPLICATIONS

This application is a continuation-in-part of U.S. patent application Ser. No. 12/248,291, filed Oct. 9, 2008 now U.S. Pat. No. 8,042,549, which claims the benefit of U.S. Provisional Application Ser. No. 61/043,644, filed Apr. 9, 2008, and this application further claims the benefit of U.S. Provisional Application Ser. No. 61/225,134, filed Jul. 13, 2009, all of which are incorporated herein by reference in their entirety.

BACKGROUND OF THE INVENTION

1. Technical Field

This invention relates generally to surgical drapes, and more particularly to surgical drapes used to cover radiological imaging equipment to maintain sterility in a surgical theatre.

2. Related Art

The need to provide a sterile environment in a surgical theatre is directly associated with the known risk of infection that can be caused by bacteria, such as from a person or surgical equipment, in the surgical theatre. As such, it is known that in order to minimize the risk of infection during a surgical procedure, it is necessary to prevent the transfer of bacteria, such as via airborne lint or dust particles, fluids, or otherwise, within the surgical theatre. Although the risks of infection caused during surgery are known, it remains a challenge to prevent their onset. Infections are estimated to affect about 2 million patients annually and result, directly or indirectly, in an estimated 100,000 deaths. Aside from the loss of life, the infections create an economic burden on hospitals. For example, some studies estimate that each bloodstream infection in a patient results in an average cost of $26,839 to the hospital. As such, to date, about 16 states have passed laws detailing how hospitals treat patients in an effort to decrease the associated risks of infection to the patients.

Surgical site infection has been estimated to occur in about 15% of clean surgeries and about 30% of contaminated surgeries. Using plastic drapes to protect the wound from organisms that may be present on the surrounding skin during surgery is one strategy used to inhibit surgical site infection. However, the current draping technique uses what is referred to as a "half sheet", which is a plain rectangular sheet of plastic material that is draped over the patient and hangs downwardly over the sides edges of an operating table. In standard operations not requiring relatively large, specialized surgical equipment, this half sheet type of drape can prove effective. However, in some cases it is necessary to introduce relatively large, unsterilized surgical equipment in the operating room (surgical theater) for use during a surgical procedure. For example, in spinal and orthopedic surgeries it is common to take radiological images of various parts of the patient's body as the surgery is being performed. The most common piece of radiological imaging equipment is a C-arm fluoroscopy unit. A C-arm obtains its name from a relatively large, generally C-shaped arm that allows the imaging portion of the unit to be swung into multiple positions desired during surgery, while the arm extends beneath and through opposite sides of the operating table. As a result, the unit has one unsterilized portion adjacent one side of the patient and another unsterilized portion adjacent an opposite side of the patient.

Given the large, arcuate shape of the C-arm fluoroscopy unit, and its mobility during use, it becomes ever so challenging to maintain sterility of the surgical theatre. Typically, though cumbersome, multiple half sheets are disposed about the unit during its use. This often results in delays of the surgical procedure and requires creativity on the part of the surgical staff in order to best deploy the sheets about portions of the unit, particularly the arm and an imaging end of the unit. The need for creativity results from the fact that there is no single accepted methodology for draping C-arm radiological units. Of course, if the half sheets are not properly deployed, then the sterility of the surgical theater is compromised, and thus, the potential for onset of infection in the patient increases. Finally, because this type of radiological equipment is moved repeatedly during surgery, even if the unit is initially draped properly, there remains an associated risk that the current draping mechanisms will become displaced, thereby exposing unsterilized portions of the unit. Accordingly, a need exists for an improved sterile drapes and method of establishing and maintaining sterility in a surgical theatre, particularly for use with relatively large, radiological imaging equipment, e.g., C-arm radiological units.

SUMMARY OF THE INVENTION

A surgical radiological C-arm imaging unit drape configured to provide a sterile outer surface about an end portion of a C-arm imaging unit includes a flexible enclosure having an upper wall with a pair of sidewalls and a rear side extending downwardly from the upper wall. The upper wall and the side walls are expandable laterally outwardly from an operating table to an expanded position and collapsible laterally inwardly toward the operating table to a collapsed position. The upper wall and the sidewalls form a pocket sized for receipt of the end portion of the imaging unit beneath the upper wall when in the expanded position. The upper wall has a sterile outer surface configured to face away from and overlie the end portion of the imaging unit to maintain sterility in a sterile zone above the operating table. The sterile outer surface is foldable inwardly and shielded from external contamination when in the collapsed position.

In accordance with another aspect of the invention, an imaging unit drape configured to provide a sterile outer surface about an end portion of a C-arm imaging unit in combination with a patient drape configured to at least partially cover a patient on a standard operating table is provided. The imaging unit drape includes a flexible enclosure having an upper wall with a pair of sidewalls and a rear side extending downwardly from the upper wall. The upper wall has an edge extending between the sidewalls with a fastener extending along the edge for attachment to the patient drape. The upper wall and the side walls are extendable laterally outwardly from the patient drape to an expanded position and collapsible laterally inwardly toward the patient drape to a collapsed position. The upper wall and the sidewalls form a pocket sized for receipt of the end portion of the imaging unit beneath the upper wall when in the expanded position. The upper wall has a sterile outer surface configured to face away from and overlie the end portion of the imaging unit to maintain sterility in a sterile zone above the operating table.

In accordance with another aspect of the invention, a combination patient drape and imaging unit drape configured to provide a sterile outer surface over a patient on a standard operating table and about an end portion of a C-arm imaging unit is provided. The combination drape includes a patient drape portion configured to overlie a patient on a standard operating table at least in part and a flexible enclosure having an upper wall with a pair of sidewalls and a rear side extending downwardly from the upper wall. The upper wall extends between the sidewalls and is extendable laterally outwardly from the patient drape portion to an expanded position and laterally inwardly toward the patient drape portion to a collapsed position. The upper wall and the sidewalls form a pocket sized for receipt of the end portion of the imaging unit beneath the upper wall when in the expanded position. The upper wall has a sterile outer surface configured to face away from and overlie the end portion of the imaging unit to maintain sterility in a sterile zone above the operating table.

In accordance with yet another aspect of the invention, a method of providing a sterile surface about an end of a C-arm imaging unit is provided. The method includes providing a flexible enclosure having an upper wall with a pair of sidewalls and a rear side extending downwardly from the upper wall wherein the upper wall and the side walls are extendable laterally outwardly to an expanded position and collapsible laterally inwardly from the expanded position to a collapsed position. Further, the upper wall and the sidewalls are provided to form a pocket beneath the upper wall when in the expanded position. The upper wall is provided having a sterile outer surface configured to face away from and overlie the end portion of the imaging unit to maintain sterility in a sterile zone above the operating table. The method further includes providing a patient drape configured to at least partially cover a patient on the operating table. Further yet, the method includes joining the flexible enclosure to the patient drape along a common edge and draping the patient drape over the desired area of the patient. Then, extending the flexible enclosure to its expanded position and rotating the end of the C-arm imaging unit upwardly into the pocket.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

DETAILED DESCRIPTION OF PRESENTLY PREFERRED EMBODIMENTS

Figure 1:
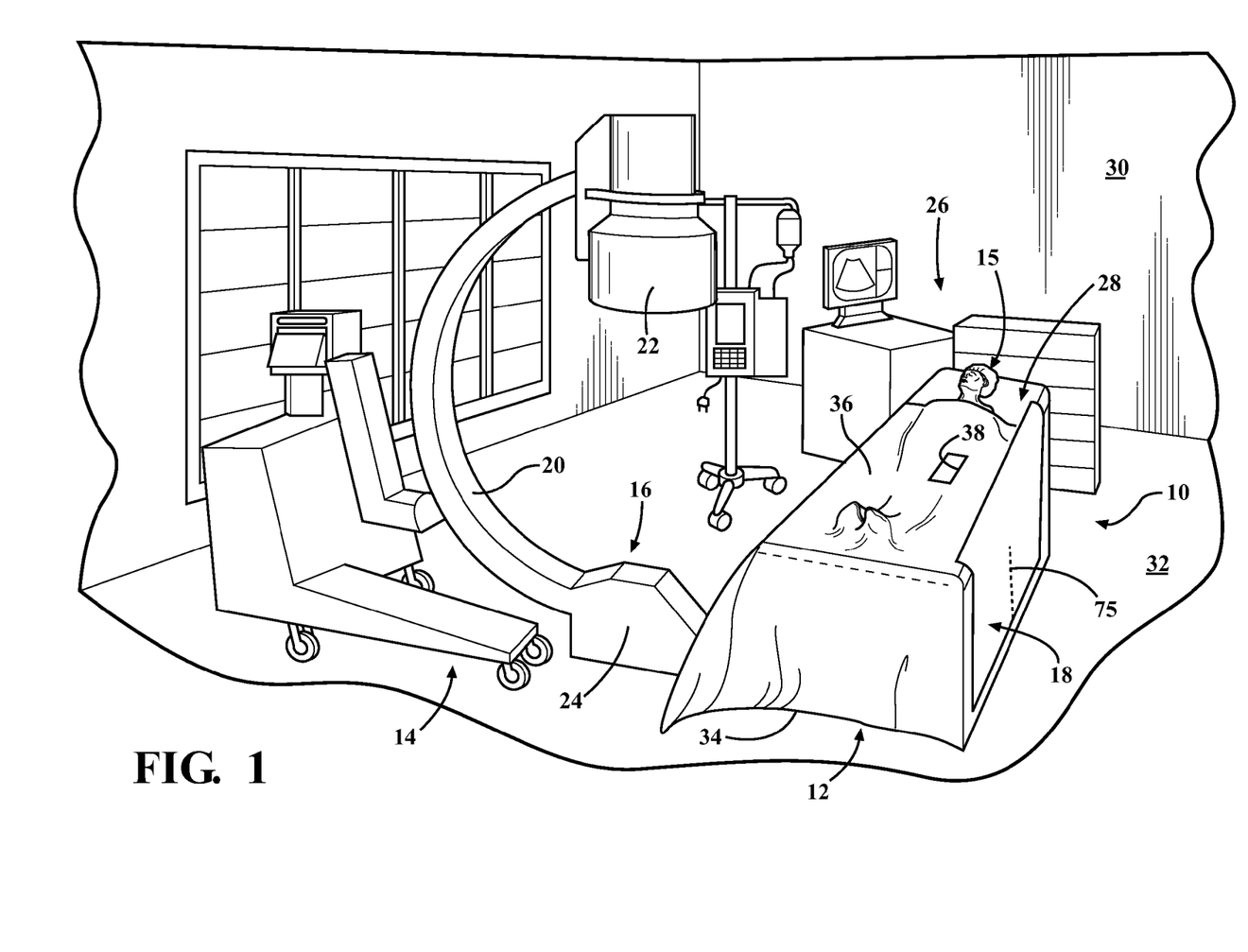
FIG. 1 illustrates a partial perspective view of a surgical theatre showing a patient on an operating table awaiting a surgical procedure requiring use of a C-arm radiological imaging unit with a standard sterile patient drape disposed over the patient and a sterile imaging unit drape constructed in accordance with one aspect of the invention attached to the patient drape in a collapsed position to provide a sterile barrier about a portion of the imaging unit to maintain sterility within the surgical theatre.

Referring in more detail to the drawings, FIG. 1 illustrates a sterile surgical C-arm radiological imaging unit drape, referred to hereafter as imaging drape 10, constructed in accordance with one aspect of the invention. The imaging drape 10 is shown attached, in a collapsed position, to a standard patient drape 12 to facilitate providing and maintaining a sterile outer surface about a portion of a C-arm type radiological imaging unit 14, and particularly about a distal end portion 16 of the imaging unit 14. The imaging drape 10 has a wall 18 providing an enclosure constructed of a flexible, tear and puncture-resistant material, such as a clear plastic material, for example, wherein the imaging drape 10 is economical in construction, and thus, is well suited to be disposed after use. The imaging drape 10 provides a quick and easy mechanism in which to reliably ensure a sterile surgical theater is maintained throughout a surgical procedure, at least with regard to a potential contamination stemming from the imaging unit 14, without having to sterilize the imaging unit 14 prior to performing the procedure. Accordingly, the imagining drape 10, in addition to performing its sterilization function, greatly reduces the potential for infection to a patient 15 in an economical manner.

The imaging drape 10 is constructed for particular use with the C-arm type radiological imaging unit 14. The C-arm type radiological unit, also referred to as a C-arm fluoroscopy unit, and referred to hereafter simply as imaging unit 14, is commonly used in surgical procedures that require multiple images to be taken of the patient from a variety of angles throughout the surgical procedure, such as a during spinal and orthopedic surgery, for example. The imaging unit 14, as the name implies, has an arcuate, generally C-shaped arm 20 that extends between a proximal, also referred to as upper, imaging head 22 and a distal, also referred to as lower, imaging head 24. The arm 20 has a sufficient length such that during the surgical procedure, the arm 20 can extend beneath a standard operating table 26 from one side of the table 26 to an opposite side of the table 26, wherein the arm 20 can be readily moved, as desired, to obtain the necessary images of the patient 15.

The patient drape 12 is configured to cover the standard operating table 26 and to hang downwardly from an upper surface 28 of the table 26. Generally, the upper surface 28 of the table 26 delineates a sterile zone 30 above the upper surface 28 and a non-sterile zone 32 below the upper surface 28. The sterile zone 30, in order to reduce risk of infection to the patient 12, must remain sterile throughout the surgical procedure, and thus, extends to all equipment positioned on or above the upper surface 28 of the surgical table 26. Accordingly, any instruments within the sterile zone 30 must either be thoroughly sterilized, such as is commonly performed with smaller surgical instruments in an autoclave, or otherwise covered with a sterile barrier.

The patient drape 12 typically has a generally rectangular peripheral shape, with free edges 34 hanging below the upper surface 28 into the non-sterile zone 32. A central area 36 of the drape 12 is configured to remain above the upper surface 28, draped in overlying relation on the patient 12. The drape 12 is commonly provided with an opening 38 located in a predetermined position, wherein the opening 38 provides direct access to an incision surgical site on the patient 12.

Figure 2:
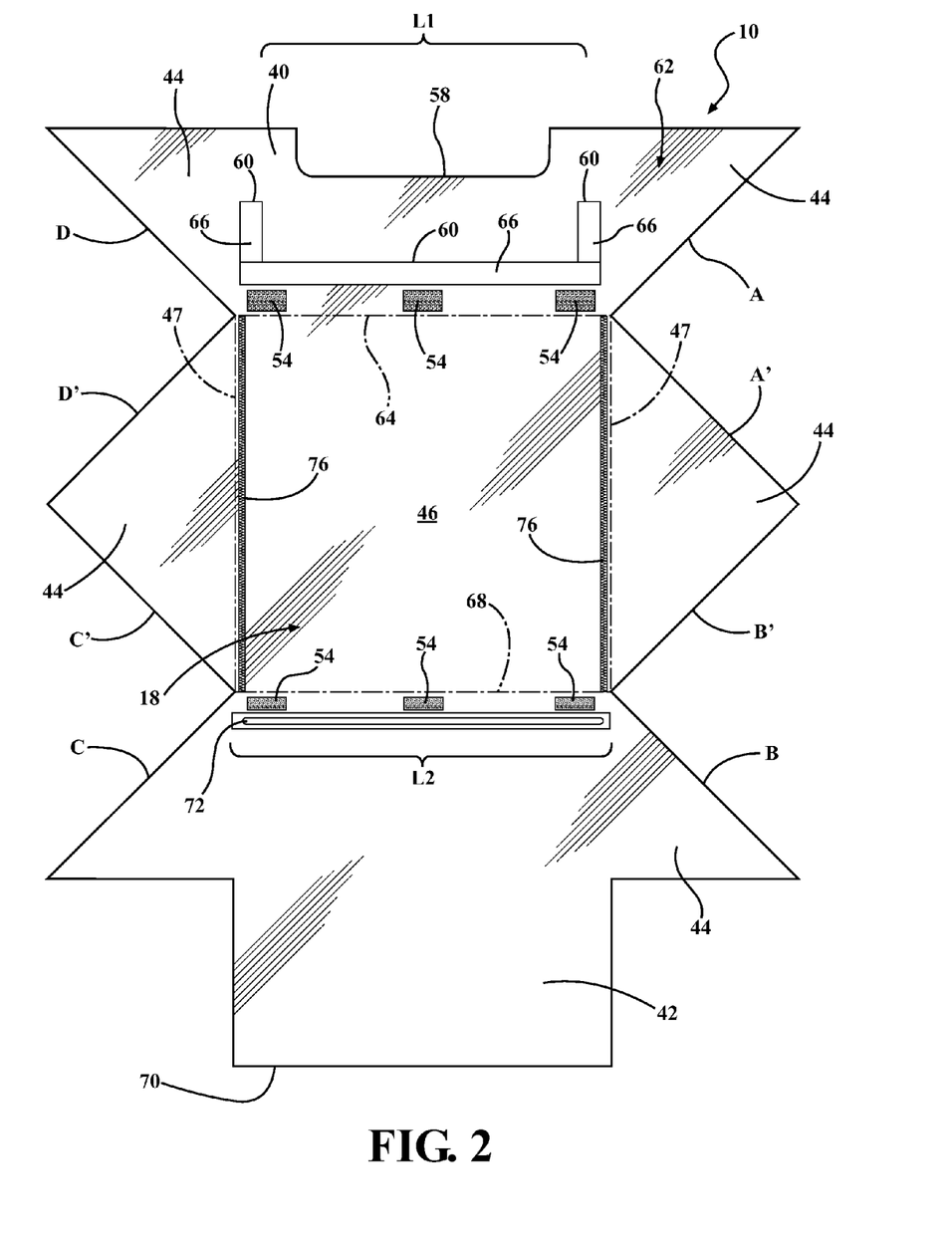
FIG. 2 illustrates a plan view of a material pattern of the imaging unit drape of FIG. 1.

As shown in FIG. 2, the wall 18 of the imaging drape 10 can be constructed as a single piece of material, or it can be formed from two or more pieces of material fixed to one another, depending on the materials used and the overall configuration desired. For example, if a plastic material is used, weld seams can be formed to join separate pieces of material to one another. Otherwise, if a textile material is used, then separated pieces of material can be stitched together, by way of example and without limitation. In the embodiment illustrated, a single piece of plastic material is formed, wherein the respective edges A, A', B, B', C, C', D, D' are joined via a weld seam to form the overall non-flat finished flexible enclosure configuration of the imaging drape 10, as discussed in detail below.

Figure 3:
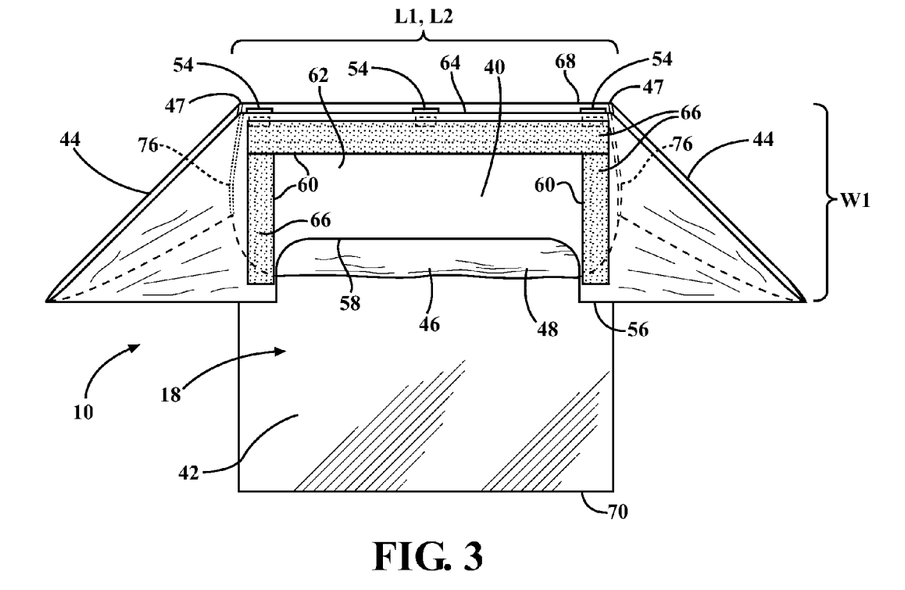
FIG. 3 illustrates a rear view of the imaging unit drape of FIG. 1 in partially collapsed and detached relation from the first drape.
Figure 4:
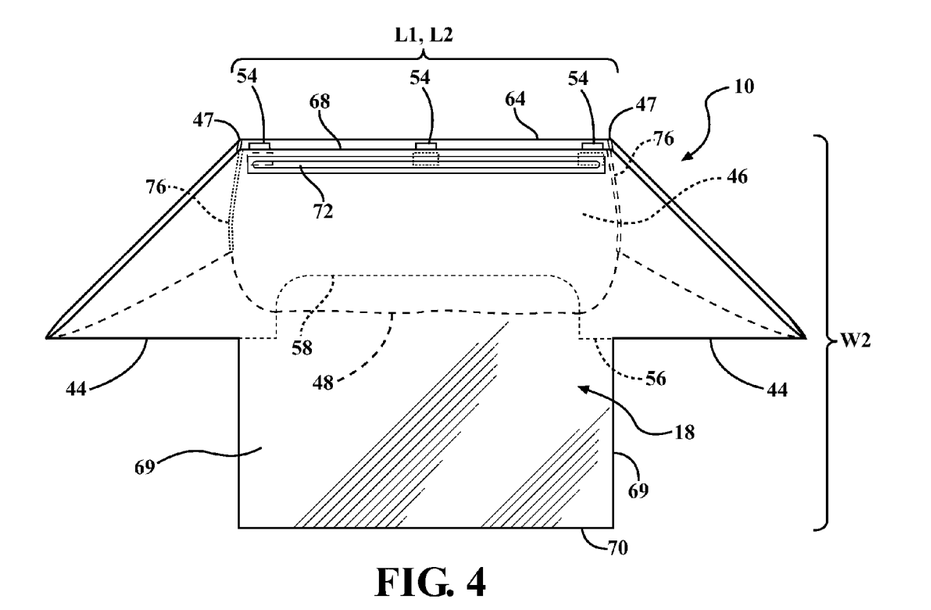
FIG. 4 illustrates a front view of the imaging unit drape of FIG. 3.
Figure 5:
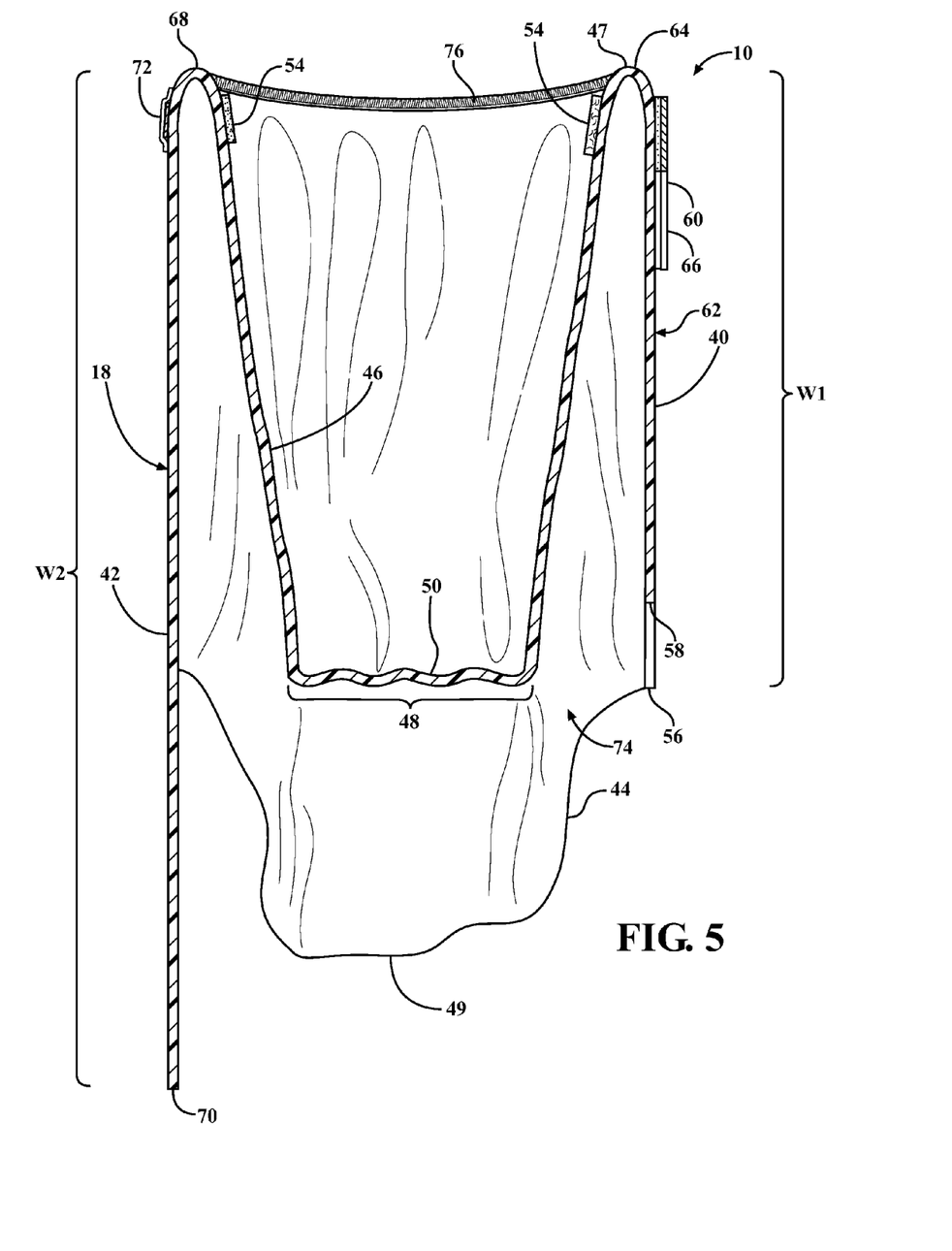
FIG. 5 illustrates a cross-sectional view taken generally along the line 5-5 of FIG. 3.
Figure 10:
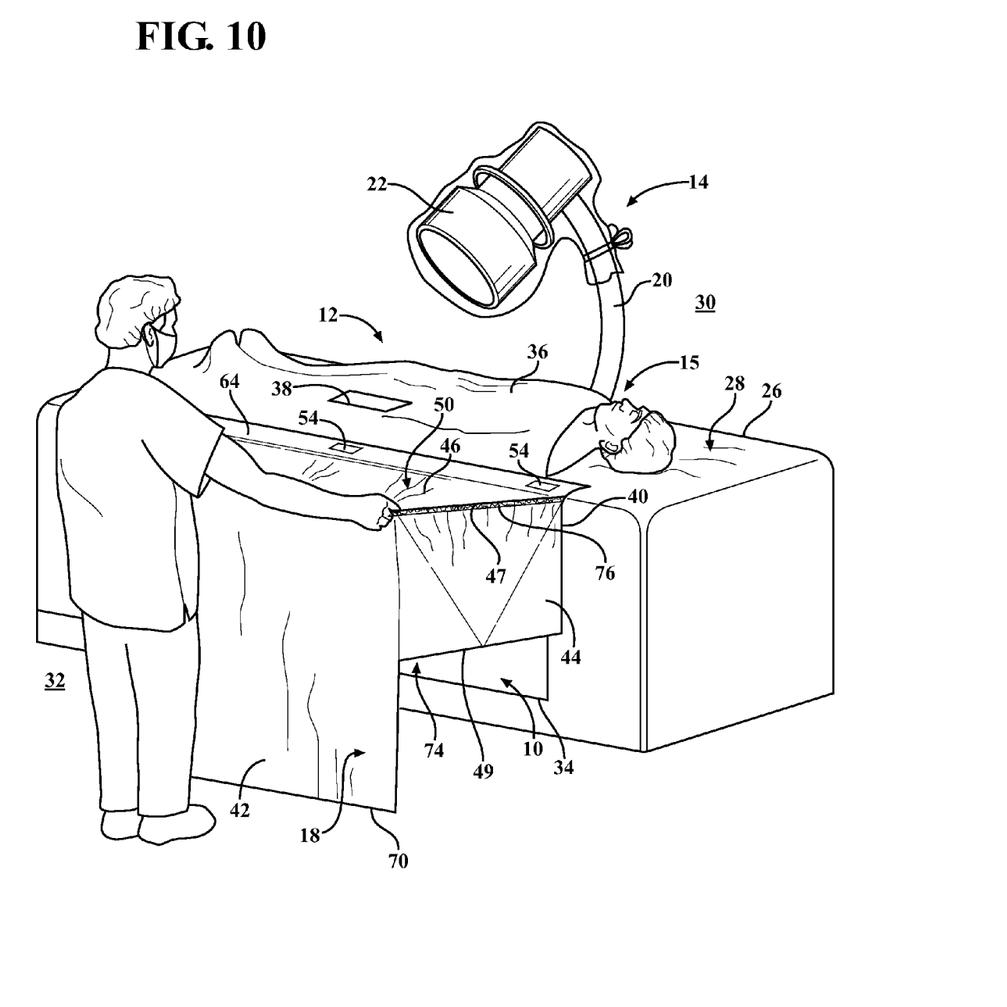
FIG. 10 illustrates a similar perspective as FIG. 9 with the imaging unit drape being further unfolded to the expanded position for receipt of a portion of the imaging unit.
Figure 11:
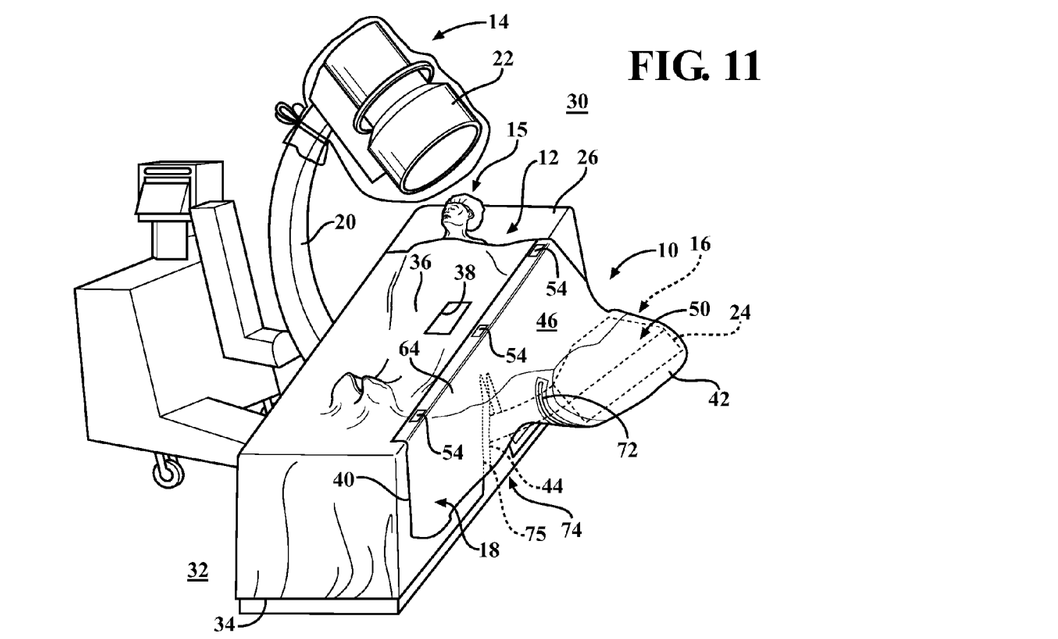
FIG. 11 illustrates perspective view showing the end of the imaging unit fully disposed within the pocket of the imaging drape in an imaging position.
Figure 12:
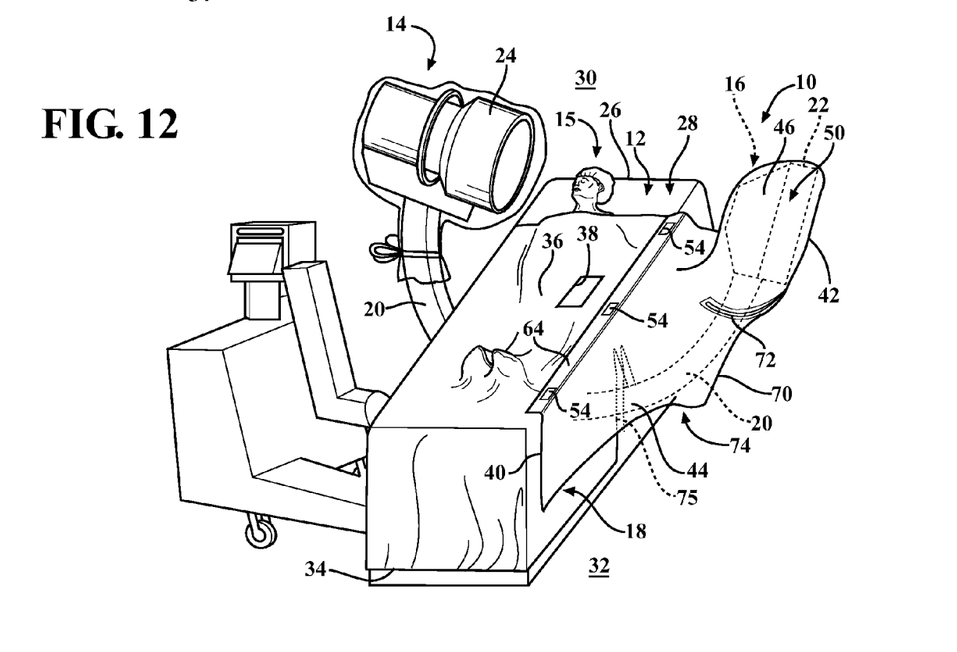
FIG. 12 illustrates a similar view as FIG. 11 showing the imaging unit positioned to a different imaging position.

As shown in FIGS. 2-5, the imaging drape 10 has a first front side 40, also referred to as proximal side or front face, and a second rear side 42, also referred to as distal side or rear face, with a pair of sidewalls 44 and an upper wall 46 extending between the front and rear sides 40, 42. As best shown in FIGS. 10 and 11, while in an unfolded configuration, the sidewalls 44 are shown, by way of example and without limitation, as extending from an upper edge 47 extending adjacent the upper wall 46 and downwardly along the full or substantially the full length of the front side 40 and along a portion of the rear side 42 to a lower free edge 49. When in a partially folded configuration, such as shown in FIGS. 3-5, the imaging drape 10 takes on a generally T-shaped configuration. The front and rear sides 40, 42 are shown folded toward one another in the collapsed position with the sidewalls 44, by way of example, having an upper portion tucked laterally inwardly in an inverted configuration and a lower portion extended laterally outwardly, thus forming the upper cross portion of the T-shape. The upper wall 46 is tucked-in downwardly between the front and rear sides 40, 42 in accordion fashion to form at least one descending pleated portion 48 sandwiched between the front and rear sides 40, 42. Although a single pleat is shown, it is contemplated that multiple pleats could be formed, if desired. The imaging drape 10 is releasably maintained in its partially folded position, with a sterile outer surface 50 of the upper wall pleated portion 48 abutting one another. While in the partially folded, collapsed position, a plurality of fasteners, such as hook and loop type fasteners 54, or any other suitable fastening mechanism, such as a self adhesive, snaps, hooks, latches, clips, zippers, or the like, are used to releasable fix the drape 10 in its folded position, until desired to unfold the drape 10 for use. Accordingly, with the fasteners 54 attached to one another, the outer surfaces 50, 52 are shielded from external contamination and maintained as sterile surfaces during handling.

The front side 40 extends along a horizontal length (L1) sufficient to extend along the full or substantially full length of the operating table 26 and has a vertically extending width (W1) sufficient to hang downwardly a predetermined distance from the upper surface 28 of the operating table 26. The width W1 is provided to allow an unobstructed deployment of the C-arm 20 and lower imaging head 24 during use, as is discussed further below. To further facilitate allowing unobstructed movement of the C-arm 20 and lower imaging head 24 during use, a lower free edge 56 of the front side 40 can be provided with a recessed, generally U-shaped cutout profile 58. Accordingly, the C-arm 20 and lower imaging head 24 are able to move freely from one side of the front side 40 to an opposing side of the front side 40 without impacting or otherwise confronting the front side 40.

As best shown in FIG. 2, to facilitate attaching the imaging drape 10 to the patient drape 12 and operably to the operating table 26, at least one, and shown here as a plurality of fasteners 60 are provided, represented as self adhesive strips applied on an outer surface 62 of the front side 40, by way of example and without limitation. It should be recognized that other types of fasteners are contemplated herein, such as hook and loop type fasteners, snaps, latches, hooks, clamps, clips, zippers, and the like. The self adhesive fasteners 60 are shown as a single strip extending substantially along the length L of the front side 40 below one portion of the fasteners 54 adjacent a common upper edge 64 of the front side 40 and upper wall 46 and a pair of shorter strips extending between the upper edge 64 and the lower free edge 56 adjacent the U-shaped profile 58. The self adhesive fasteners 60 are preferably covered with a release paper 66, such that the release paper 66 can be selectively removed during deployment to expose the respective self adhesive fasteners 60 for attachment to the patient drape 12 or operating table 26, as desired.

As best shown in FIG. 4, the rear side 42 has an upper edge 68 that extends over a horizontal length (L2) between opposite sides 69 that is the same or substantially the same as the length L1 of the front side 40. Further, the rear side 42 has a vertically extending width (W2) that is greater than W1 of the front side 40. As such, the overall configuration of the imaging drape 10 is asymmetrical. The width W2 of the rear side 42 is sufficient to hang downwardly a predetermined distance from the upper surface 28 of the operating table 26 to ensure that the C-arm 20 and lower imaging head 24 remain fully covered and shielded by the imaging drape 10 over the full range of potential movement of the imaging unit 14. Further, another portion of the fasteners 54 on the rear side 42 are positioned adjacent the upper edge 68 in mirrored positions suitable from releasable attachment to the corresponding fasteners 54 on the front side 40.

To facilitate forming the imaging drape 10 about the lower imaging head 24, which in turn keeps the imaging drape 10 properly disposed about the imaging head 24 and prevents the imaging drape 10 from slipping or falling off the imaging head 24 below the sterile zone 30, a structural, formable member 72 extends along at least a portion of the rear side 42. The formable member 72 is shown here, by way of example and without limitation, as extending along the full or substantially full length L2 adjacent the upper edge 68. The formable member 72 can be provided as any semi rigid, plastically formable support member, such as, by way of example, a strip of metal or foil that can be plastically deformed by hand. Although shown as a single piece of formable material, it should be recognized that the formable member 72 can be provided as two or more separate members in attached relation, with one another via hinges or otherwise, or in spaced relation from one another, as desired. Further, the formable member 72 can be provided having a predetermined memory shape, such that when externally applied handling forces are release, the formable member 72 retains its predetermined memory shape, such as is commonly performed via Nitinol, for example. The formable member 72 can be attached to an external surface of the rear side 42 via any suitable adhesive, tape, stitching, or other type of fastener, or it can be disposed in a preformed elongate pocket or slot in the rear side 42, for example. In addition, the formable member 72 can be provided as a clear material or having any chosen color to facilitate visualization of the member 72. In addition to providing the forming function, the formable member 72 can also act as a handle and/or to identify an appropriate sterile location to grasp the drape while the C-arm 20 is being moved from one location to another. Further yet, the formable member 72 can also be provided to extend along or adjacent a lower free edge 70, wherein the formable member 72, or other weighted mechanism, can function to maintain the non-sterile portions of the imaging drape 10 in the intended hanging position within the non-sterile zone 32 to avoid obstructing the surgical team during surgery and to prevent the non-sterile portions from entering the sterile zone 30.

Figure 10A:
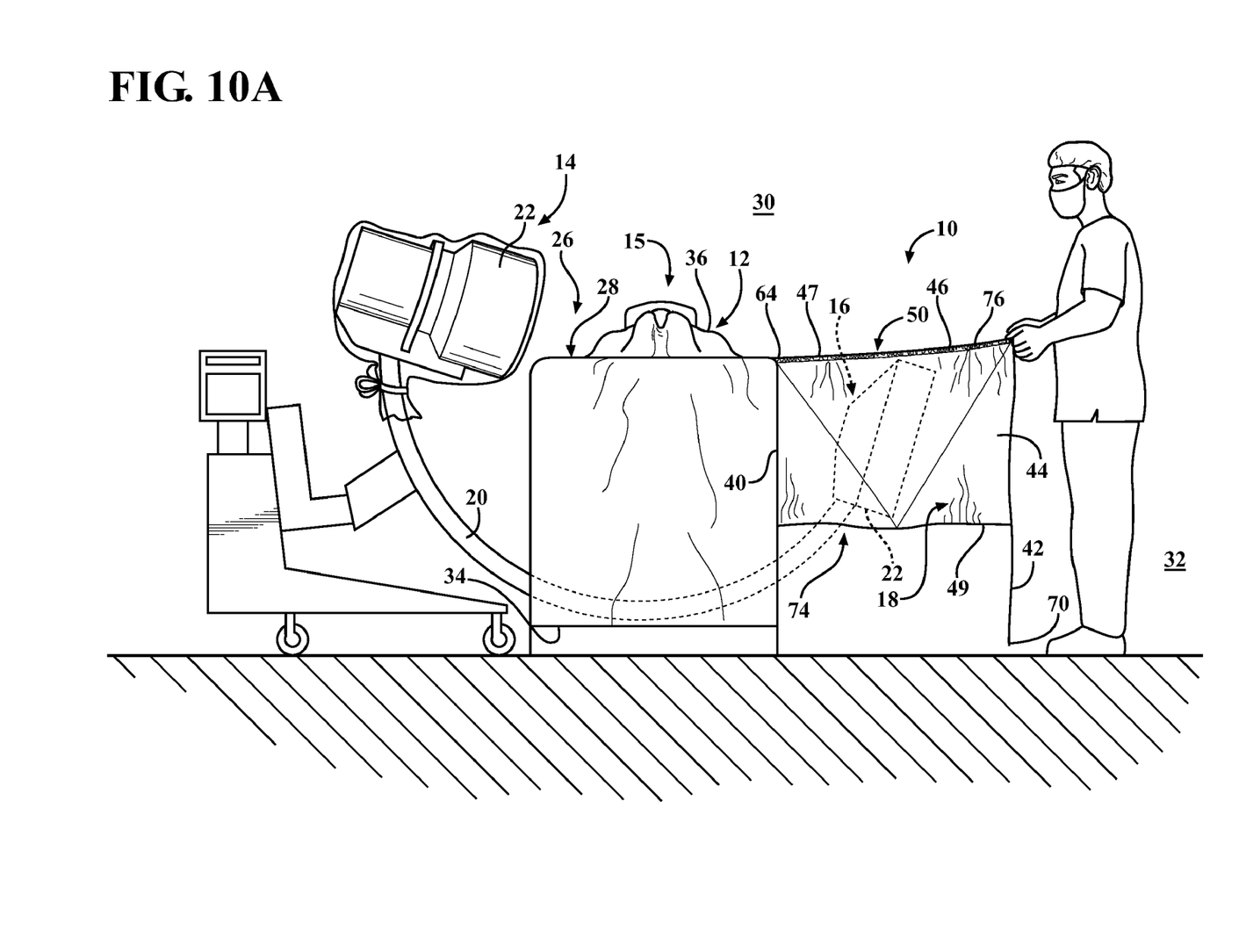
FIG. 10A is a side view of FIG. 10 showing an end of the imaging unit being disposed beneath the operating table into an unfolded pocket of the imaging drape.

The upper wall 46 extends between the front side upper edge 64 and the rear side upper edge 68 and between the upper edges 47 of the sidewalls 44. As previously mentioned, the outer surface 50 is provided and maintained as a sterile surface, both in storage and in use. The upper wall 46, in combination with the front side 40, rear side 42 and sidewalls 44 form a "domed" pouch, also referred to as pocket 74, directly underlying the upper wall 46 when in an expanded position (FIGS. 10 and 10A). The pocket 74 is sized for receipt of the lower imaging head 24, as discussed further hereafter. Upon disposing the lower imaging head 24 within the pocket 74, to facilitate maintaining the imaging drape 10 in its intended position throughout the procedure, in addition to or in lieu of the formable member 72, a pair of elastic members 76 are preferably provided, shown here as extending along the sidewalls 44 along or adjacent the upper edges 47. The elastic members 76 can be provided as any suitable elastic cord, band or otherwise, and are operably fixed to predetermined locations of the sidewalls 44, such as via stitching, adhesive, fasteners, or otherwise.

In use, and in accordance with a method of providing a sterile surface about a portion of an imaging unit 14, the patient drape 12 is disposed over the patient and operating table 26 to located the opening 38 over the intended incision location on the patient. If the patient drape extends below the non-sterile zone in the area through which a C-arm 20 will be moved, then the wall of the patient drape 12 can be cut, such as by making a vertically extending, centrally located slit 75 through the patient drape wall centrally between the opposite ends of the operating table 26 from a predetermined height to the lowermost free edge of the drape 12.

Figure 6:
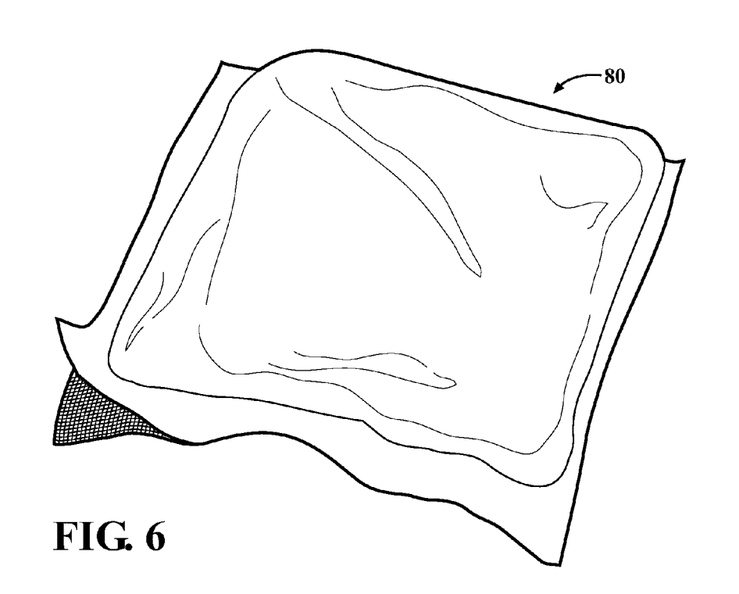
FIG. 6 illustrates the imaging unit drape of FIG. 1 shown folded and stored in a sterile package.
Figure 7:
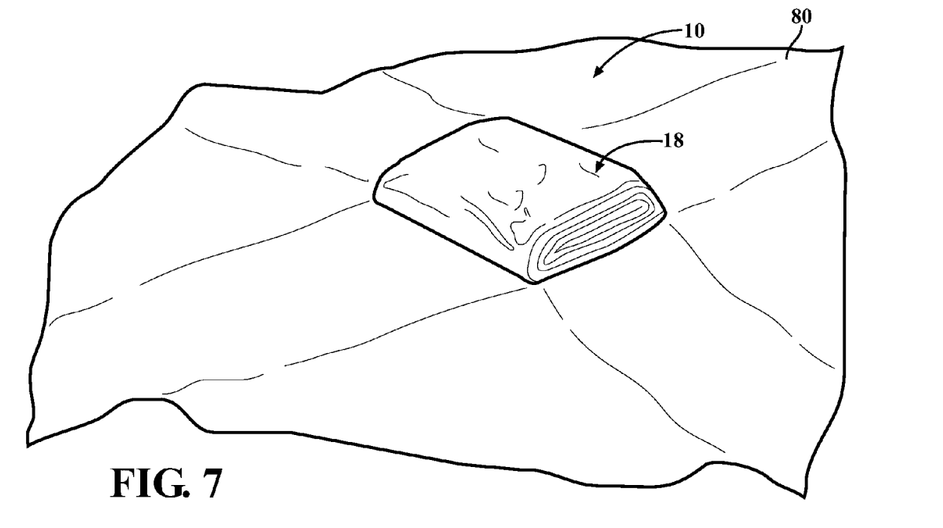
FIG. 7 illustrates the package of FIG. 6 opened with the imaging unit drape in a predetermined folded state.
Figure 8:
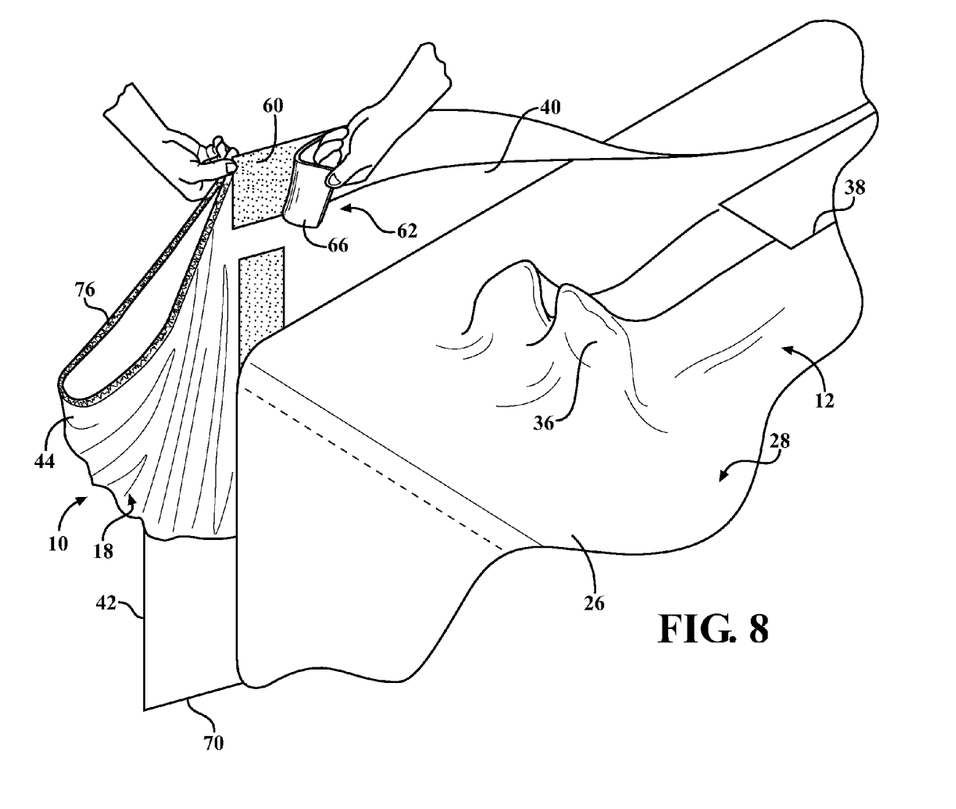
FIG. 8 illustrates the imaging unit drape being attached to the patient drape on the operating table.

Next, the imaging drape 10 is removed from a sterile package 80 (FIGS. 6 and 7) and unrolled to expose the fasteners 60 on the front side 40. Then, as shown in FIG. 8, the release paper 66 is removed and the underlying adhesive fasteners 60 are fixed to the patient drape 12, or operating table 26, adjacent a lengthwise extending edge of the operating table 26 and along a hanging portion of the patient drape 12. Upon completing this step, the imaging drape 10 preferably remains in its collapsed position until the following step is performed.

Figure 9:
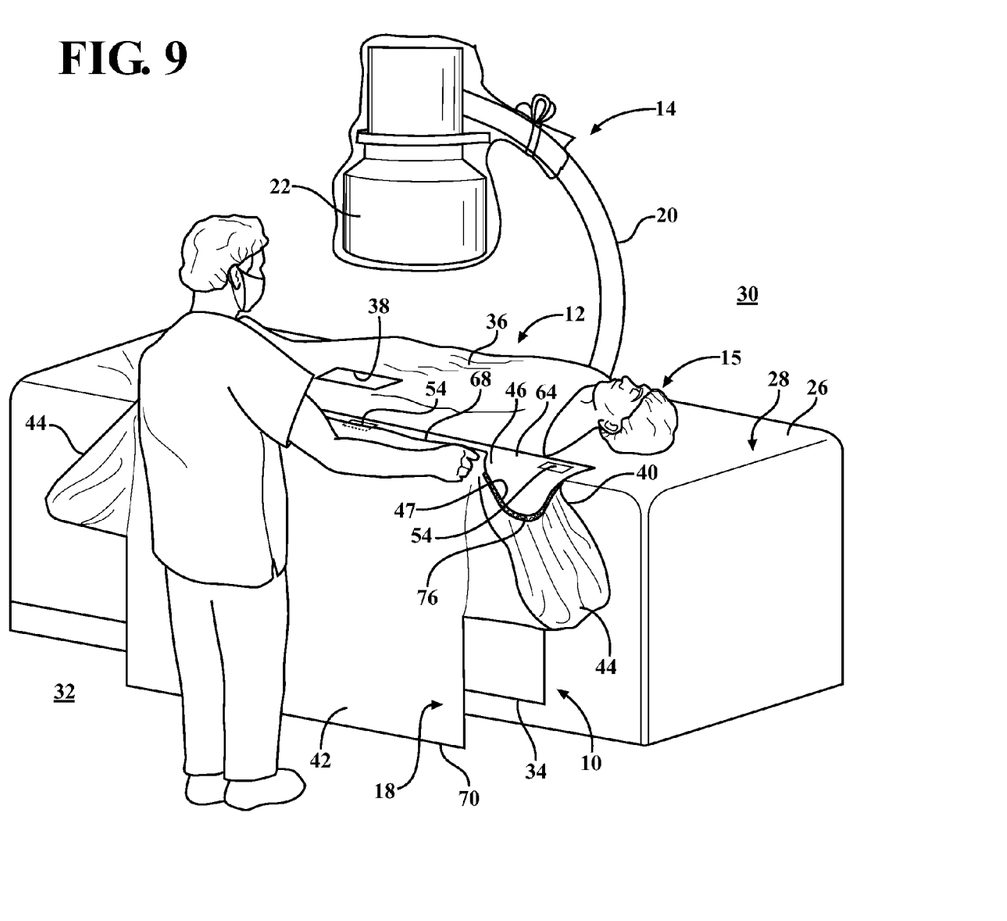
FIG. 9 illustrates the imaging unit drape being initially unfolded from the collapsed position toward an expanded position in preparation for receipt of a portion of the imaging unit.

Further, as shown in FIG. 9, with the imaging drape 10 attached to the patient drape 12, the rear side upper edge 68 is detached from the front side upper edge 64 by separating the respective fasteners 54. Then, as shown in FIG. 10, the rear side 42 is pulled and expanded laterally outwardly away from the operating table 26, during which time the elastic members 76 are biased into an extended position by the externally applied pulling force and the pleated portion 48 of the upper wall 46 is caused to unfold upwardly. Upon the upper wall 46 being raised into its expanded, unfolded position, the pocket 74 is formed for receipt of the lower imaging head therein and the drape 10 is now in its fully expanded position.

As such, as shown in FIG. 10A, upon unfolding the pleated portion 48 to the expanded position, the lower imaging head 24 can be freely swung beneath the operating table 26, through the slit 75 (if necessarily formed) in the patient drape 12, and into the domed pocket 74.

Then, as shown in FIG. 11, the rear side 42 can be released, whereupon the elastic members 76 automatically retract absent the externally applied biasing force, thus drawing the upper edge 68 of the rear side 42 laterally inwardly from the fully expanded position and into abutment with a selected portion of the lower imaging head 24 to a partially expanded position. At this time, the sterile outer surface 50 of the upper wall 46 is draped over the lower imaging head 24 and the rear side 42 hangs downwardly therefrom. In addition, to further maintain the imaging drape 10 in its intended draped position on the lower imaging head 24, the formable member 72 can be plastically deformed by hand about a selected portion of the lower imaging head 24, thus, inhibiting any unwanted movement or slippage of the imaging drape 10 relative to the lower imaging head 24.

Upon operably attaching the imaging drape 10 to the operating table 26, such as by fixing it to the patient drape 12, by way of example, and disposing the lower imaging head 24 within the unfolded pocket 74, the lower imaging head 24 can be moved in over its multi-axes degrees of movement, as needed to obtain the desired images, the imaging drape 10 maintains a sterile outer surface within the sterile zone 30. Accordingly, the potential for infection resulting from the use of the imaging unit 14 is negated, or at the very least, minimized.

Figure 13:
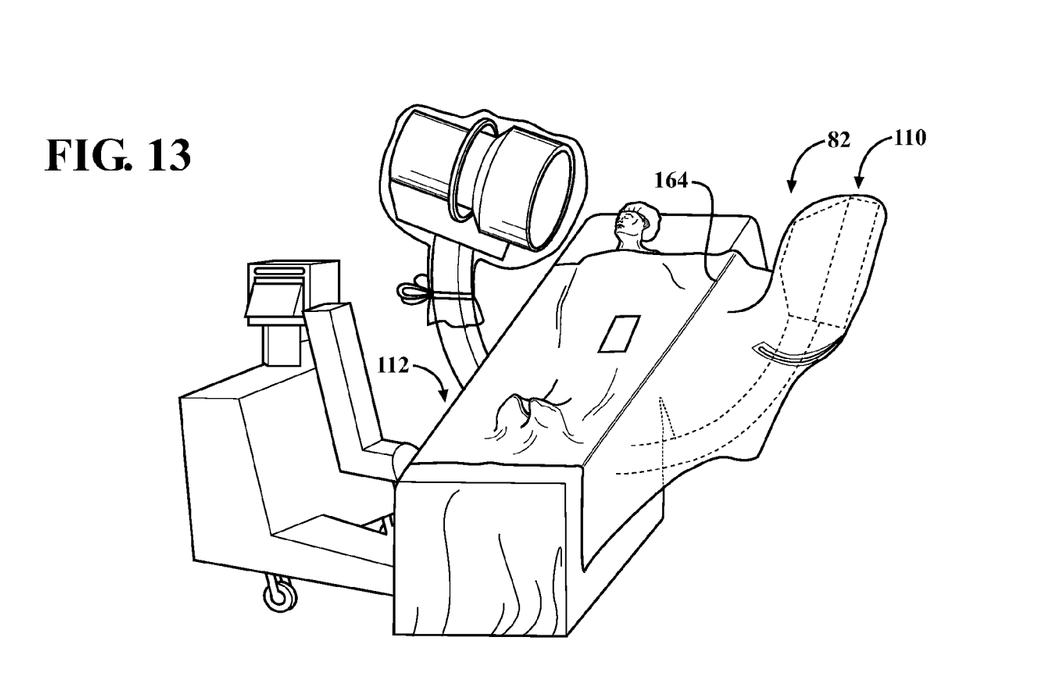
FIG. 13 illustrates a perspective view similar to FIG. 12 of a sterile imaging drape constructed in accordance with another aspect of the invention.

In FIG. 13, a combination patient drape/imaging drape 82 constructed in accordance with another aspect of the invention is shown, wherein the same reference numerals used above, offset by a factor of 100, are used to identify like features.

The patient drape/imaging drape 82 is a structural combination of the patient drape 12 and the imaging drape 10 discussed above. As such, rather than having a separate patient drape and imaging drape, the patient drape/imaging drape 82 is a constructed as a single or substantially single piece of material, having a patient drape portion 112 and an imaging drape portion 110 joined along a common edge 164. Accordingly, it should be recognized that a single piece of material can be used to form the patient drape/imaging drape 82, or two or more pieces may be fixed together, such as via weld seams, stitching, adhesives, tapes, or otherwise, along the common edge 164. Otherwise, the patient drape/imaging drape 82 performs the same functions as discussed above with regard to the separate imaging drape 10 and the patient drape 12.

Obviously, many modifications and variations of the present invention are possible in light of the above teachings. It is, therefore, to be understood that within the scope of the appended claims, the invention may be practiced otherwise than as specifically described.

What is claimed is:

1. A surgical radiological C-arm imaging unit drape configured to provide a sterile outer surface about an end portion of a C-arm imaging unit, comprising:

a flexible enclosure having an upper wall with a pair of sidewalls and a rear side extending downwardly from said upper wall, said upper wall and said side walls being expandable laterally outwardly from an operating table to an expanded position and laterally inwardly from said expanded position toward the operating table to a collapsed position, said upper wall and said sidewalls forming a pocket sized for receipt of the end portion of the imaging unit beneath said upper wall when in said expanded position, said upper wall having a sterile outer surface configured to face away from and overlie the end portion of the imaging unit to maintain sterility in a sterile zone above the operating table, said sterile outer surface being folded inwardly and shielded from external contamination when in said collapsed position.

2. The surgical radiological C-arm imaging unit drape of claim 1 wherein said upper wall has an edge extending between said sidewalls and further comprising a fastener extending along said edge, said fastener being configured for operable attachment to the operating table.

3. The surgical radiological C-arm imaging unit drape of claim 1 further comprising a front side opposite said rear side, said front side being attached to said sidewalls and said upper wall and forming a portion of said pocket.

4. The surgical radiological C-arm imaging unit drape of claim 3 wherein said front side and said upper wall have a common edge and further comprising a fastener extending along said edge, said fastener being configured for operable attachment to the operating table.

5. The surgical radiological C-arm imaging unit drape of claim 4 wherein said fastener is a self adhesive.

6. The surgical radiological C-arm imaging unit drape of claim 4 wherein said fastener is attached to said front side.

7. The surgical radiological C-arm imaging unit drape of claim 3 wherein said front side and said rear side extend downwardly from said upper wall over a width, said width of said front side being different from said width of said rear side.

8. The surgical radiological C-arm imaging unit drape of claim 7 wherein said width of said front side is less than said width of said rear side.

9. The surgical radiological C-arm imaging unit drape of claim 3 wherein said front side has a cutout U-shaped portion extending between said sidewalls.

10. The surgical radiological C-arm imaging unit drape of claim 1 wherein said upper wall has an upper edge and said rear side has an upper edge and further comprising at least one fastener configured to releasably fix said upper edge of said upper wall to said upper edge of said rear side when in said collapsed position.

11. The surgical radiological C-arm imaging unit drape of claim 10 further comprising a formable member extending along said upper edge of said rear side, said formable member being plastically deformable by hand.

12. The surgical radiological C-arm imaging unit drape of claim 1 further comprising an elastic member extending along each of said sidewalls, said elastic member biasing said sidewalls from said expanded position toward said collapsed position.

13. An imaging unit drape configured to provide a sterile outer surface about an end portion of a C-arm imaging unit in combination with a patient drape configured to at least partially cover a patient on a standard operating table, said imaging unit drape comprising:
a flexible enclosure having an upper wall with a pair of sidewalls and a rear side extending downwardly from said upper wall, said upper wall having an edge extending between said sidewalls with a fastener extending along said edge for attachment to said patient drape, said upper wall and said side walls being extendable laterally outwardly from the patient drape to an expanded position and laterally inwardly from said expanded position toward the patient drape to a collapsed position, said upper wall and said sidewalls forming a pocket sized for receipt of the end portion of the imaging unit beneath said upper wall when in said expanded position, said upper wall having a sterile outer surface configured to face away from and overlie the end portion of the imaging unit to maintain sterility in a sterile zone above the operating table.

14. The combination of claim 13 wherein said imaging unit drape further comprises a front side opposite said rear side, said front side being attached to said upper wall along said edge and forming a portion of said pocket.

15. The combination of claim 14 wherein said fastener is a self adhesive.

16. The combination of claim 15 wherein said fastener is attached to said front side.

17. The combination of claim 14 wherein said front side and said rear side extend downwardly from said upper wall over a width, said width of said front side being different from said width of said rear side.

18. The combination of claim 13 wherein said rear side has an upper edge and further comprising at least one fastener configured to releasably fix said edge of said upper wall to said upper edge of said rear side when in said collapsed position, said upper wall forming at least one pleat when in said collapsed position.

19. The combination of claim 18 further comprising a formable member extending along said upper edge of said rear side, said formable member being plastically deformable by hand.

20. The combination of claim 13 further comprising an elastic member extending along each of said sidewalls, said elastic member biasing said sidewalls from said expanded position toward said collapsed position.

21. A combination patient drape and imaging unit drape configured to provide a sterile outer surface over a patient on a standard operating table and about an end portion of a C-arm imaging unit, said imaging unit drape comprising:
a patient drape portion configured to overlie a patient on a standard operating table at least in part; and
a flexible enclosure having an upper wall with a pair of sidewalls and a rear side extending downwardly from said upper wall, said upper wall extending between said sidewalls and being extendable laterally outwardly from said patient drape portion to an expanded position and laterally inwardly toward said patient drape portion to a collapsed position, said upper wall and said sidewalls forming a pocket sized for receipt of the end portion of the imaging unit beneath said upper wall when in said expanded position, said upper wall having a sterile outer surface configured to face away from and overlie the end portion of the imaging unit to maintain sterility in a sterile zone above the operating table.

22. The combination patient drape and imaging unit drape of claim 21 wherein said upper wall and said patient drape have a common edge and said rear side has an upper edge and further comprising at least one fastener configured to releasably fix said common edge to said upper edge when in said collapsed position.

23. The combination patient drape and imaging unit drape of claim 22 further comprising a formable member extending along said upper edge of said rear side, said formable member being plastically deformable by hand.

24. The combination patient drape and imaging unit drape of claim 21 further comprising an elastic member extending along each of said sidewalls, said elastic member biasing said sidewalls from said expanded position toward said collapsed position.

25. A method of providing a sterile surface about an end of a C-arm imaging unit, comprising:
    providing a flexible enclosure having an upper wall with a pair of sidewalls and a rear side extending downwardly from the upper wall wherein the upper wall and the side walls are extendable laterally outwardly to an expanded position and collapsible laterally inwardly from the expanded position to a collapsed position, wherein the upper wall and the sidewalls form a pocket beneath the upper wall when in the expanded position, said upper wall having a sterile outer surface configured to face away from and overlie the end portion of the imaging unit to maintain sterility in a sterile zone above the operating table;
    providing a patient drape configured to at least partially cover a patient on the operating table;
    joining the flexible enclosure to the patient drape along a common edge;
    draping the patient drape over the desired area of the patient;
    extending the flexible enclosure to its expanded position; and
    rotating the end of the C-arm imaging unit upwardly into the pocket.

26. The method of claim 25 further including providing the patient drape and the imaging drape as separate pieces of material.

27. The method of claim 26 further including joining the imaging drape to the patient drape via a fastener.

28. The method of claim 26 further including extending the flexible enclosure to its expanded position against a bias imparted by an elastic member and allowing the flexible closure to return toward the collapsed position under the bias after rotating the end of the C-arm imaging unit upwardly into the pocket.

29. The method of claim 26 further plastically deforming a formable member of the imaging drape about the end of the C-arm imaging unit after rotating the end of the C-arm imaging unit upwardly into the pocket.

* * * * *